United States Patent [19]

Miller, Jr.

[11] 4,178,363
[45] Dec. 11, 1979

[54] METHOD FOR REDUCING DENTAL PLAQUE AND PELLICLE PRECURSOR OF PLAQUE

[76] Inventor: Taylor C. Miller, Jr., 210 Professional Center, Montgomery, Ala. 36104

[21] Appl. No.: 904,335

[22] Filed: May 9, 1978

[51] Int. Cl.² .......................... A61K 7/16; A61K 7/24; A61K 31/20
[52] U.S. Cl. ....................................... 424/49; 424/55; 424/318
[58] Field of Search ................................... 424/49–58, 424/318

[56] References Cited

U.S. PATENT DOCUMENTS

| | | | |
|---|---|---|---|
| 2,510,946 | 6/1950 | Baker | 424/318 X |
| 3,476,854 | 11/1969 | Molnar | 424/78 |
| 4,082,841 | 4/1978 | Pader | 424/50 |

Primary Examiner—Shep K. Rose

Attorney, Agent, or Firm—Clarence A. O'Brien; Harvey B. Jacobson

[57] ABSTRACT

A method for reducing dental plaque and infections of the teeth, gums, and mouth, the present invention essentially comprises application of an effective amount of n-undecylenic acid or an effective substitute therefor according to the invention to the teeth, gums and mouth. The effective ingredient employed according to the method of the invention can either be applied directly to the teeth and tissues in a substantially inert carrier such as in a dentifrice paste for personal oral use or can be applied directly by a dental practitioner. Practice of the present method improves the condition of the gums and other tissues of the mouth, acts to prevent yeast and other infections, reduces the incidence of tooth decay caused by parasitic bacteria, reduces the bacteria count in the mouth to provide a more hygienic oral environment, substantially reduces plaque formation present on the teeth prior to treatment according to the invention, and essentially acts to prevent new plaque from forming on the teeth with continued treatment.

1 Claim, No Drawings

METHOD FOR REDUCING DENTAL PLAQUE AND PELLICLE PRECURSOR OF PLAQUE

BACKGROUND OF THE INVENTION

1. Field of the Invention

The invention generally relates to treatment methods for the improvement of the health of the teeth, gums, and mouth, the invention particularly providing methods for the reduction and prevention of pellicle and plaque on the teeth and of infections of the teeth, gums, and mouth.

2. Description of the Prior Art

Proper oral hygiene as presently practiced requires that the substance known as "plaque" which forms on the surfaces of the teeth be removed in order to eliminate a source of potential injury to the teeth and gums as well as to allow usual oral hygiene methods to be more effective. The removal of plaque is, therefore, not for cosmetic purposes although such purposes are also served when plaque is removed from the teeth. Prior methods for removing plaque have essentially been mechanical in nature, the toothbrush being used for personal hygiene by the patient. Abrasive compounds are also applied by the dentist to the teeth by rotary "polishing" instruments which mechanically "scour" plaque from the teeth. These prior treatments, while effective, at best only eliminate the gross build-up on the teeth, thin layers of plaque remaining after such treatments due to the undesirability of grinding or abrading the enamel surfaces of the teeth which can result from a too enthusiastic practice of the prior methods.

The necessity for plaque control is due to the very nature of this rather complex material. Essentially, pellicle, a precursor of plaque, deposits in rough areas or at or under the free margin of the gingiva. Plaque is generally considered to be a deposit of material on the surface of a tooth, the deposit usually is a growth of bacteria. Plaque also acts as a nucleus for formation of a dental calculus which typically comprises calcium phosphate, calcium carbonate, and organic matter which forms as a deposit on the surface of the teeth. Plaque has different forms and combinations of forms depending on individual oral conditions, the syndrome typically referred to as plaque usually not being recognized as having the complexity which it exhibits. The complex nature of plaque is elucidated only partially by an appreciation of the fact that plaque can be at least partially bacterial and/or fungal in nature as well as being an actual deposit of inorganic and organic materials. The very complexity of the syndrome referred to as plaque has caused the dental practitioner to feel the need for even more effective treatment and preventative tools than have heretofore been available. The present invention provides such a tool and, concurrently, provides treatment methods otherwise useful for generally treating oral infections, including yeast infections, and for maintaining a high level of oral health. In particular, practice of the present invention acts to reduce tooth decay and gum diseases inter alia by reducing the bacteria count in the mouth, the reduction of the bacteria count to a desired and safe level due to the present methods being one cause for the reduction of tooth decay and gum diseases provided by the invention.

When considering the prior art at the time of the present invention, U.S. Pat. No. 3,476,854 to Molnar is to be noted. Molnar discloses a dental plastic composition which includes a fatty acid, such as undecylenic acid, as a bound portion of the plastic polymer, the acid not being capable of leaching out of the plastic composition. Therefore, when the dental plastic composition is utilized as intended by Molnar to fabricate dentures, the action of saliva or other oral fluids do not cause the acid or other equivalent substance of Molnar to leach from the denture. Molnar clearly intends to maintain the acid within the dental plastic composition and indicates that his composition would be frustrated in its intended purpose were the acid to so vacate the composition. The bound acid or other active ingredient in the denture formed according to the teachings of Molnar acts to prevent the formation of the pathologic fungus *Candida albicans* on and in the denture. Molnar provides no indication that undecylenic acid could be directly applied to the teeth and tissues of the mouth to reduce or eliminate plaque on the teeth or to treat infections of the gums and other tissues due to bacteria. Molnar does not envision improvement of the condition of the gums, teeth and mouth by reduction of the bacteria count in the mouth as well as by the prevention and/or treatment of yeast infections and fungal conditions in the mouth. Molnar clearly does not provide any indication that tooth decay due to the presence of parasitic bacteria in the mouth can be treated, reduced, and/or prevented through the use of undecylenic acid or any other substance, composition of matter, or treatment.

Fatty acids, such as undecylenic acid, have also been previously used for the control of fungus infections in the intestine as well as in plastics as a plasticizer, as a flavoring, and as a constituent of perfumes and lubricants. As a further example of a use of such fatty acids, Jones et al., in U.S. Pat. No. 2,396,012, disclose a method for repelling insects comprising the application of such acids to the skin, clothing, or other areas from which the insects are to be repelled. The prior art has not, however, provided the unexpected results and advantages which accrue from a practice of the present invention.

SUMMARY OF THE INVENTION

The present invention provides methods for reducing dental plaque and infections of the teeth, gums, and mouth, a preferred method according to the invention comprising the step of applying an effective amount of n-undecylenic acid or a non-toxic salt thereof including the calcium and zinc salts to the teeth and mouth tissues, particularly the gums. While n-undecylenic acid and the calcium and zinc salts thereof are particularly useful according to the invention, it is to be understood that the saturated form of n-undecylenic acid, i.e., undecanoic acid and the non-toxic salts thereof, are also useful in a similar fashion. Monocarboxylic fatty acids which also show a satisfactory utility according to the invention are propionic, caprylic, and caproic acids, the non-toxic salts thereof being also useful to a satisfactory degree. It is to be understood that the use of the term undecylenic acid is taken to include the salts thereof as aforesaid and the monocarboxylic acids indicated hereinabove as well as the non-toxic salts thereof. It is also to be appreciated that the straight-chain, partially unsaturated n-undecylenic acid provides particularly effective results when used according to the teachings of the present invention.

Undecylenic acid can be utilized according to the invention in a dentifrice normally applied to the teeth and gums on a daily basis. In such a composition, the total weight proportion of the acid and/or salt thereof or any combination of acids and/or salts is typically less than 5%, the balance of the dentrifice composition comprising a mild dentifrice paste such as Kolynos paste or any dentifrice with or without abrasives or active ingredients other than the substances added to the dentifrice according to the invention. While the acids and/or salts could be used in such a dentifrice in weight proportions greater than 5%, and are so used for relatively shorter periods of time to correct certain situations, the taste of the composition according to the invention becomes objectionable to many individuals after a period of time. The method of the present invention is preferably practiced with a dentifrice composition which does not contain fluoride. The present methods can also be practiced with oral irrigating devices, effective concentrations of undecylenic acid being even less than 0.01% by weight of the irrigating solution. In the concentrations indicated for use in a dentifrice or with an oral irrigating device, the method of the invention can be practiced indefinitely without irritation of the tissues or loss of tooth structure, the practice of the present method acting to forcefully deter infections of the gums and to also deter the incidence of tooth decay due at least in part to the reduction and/or elimination of plaque on the teeth.

The present method can also be practiced by a dental practitioner, the preferred method so employed comprising a topical application of undecylenic acid to the teeth, gums, and at least contact by the acid with oral tissues, the acid being applied even in full strength for rapid reduction of plaque and stubborn parasitic infections or infestations including fungus and yeast infections. Such full-strength application is preferably followed by oral irrigation. Topical application by a dental practitioner typically utilizes a given weight proportion of undecylenic acid in an otherwise or essentially inert application medium, the weight percent of undecylenic acid typically being 10 to 50% in such a composition.

It is, therefore, an object of the present invention to provide methods for at least reducing dental plaque on the teeth and infections of the teeth, gums, and tissues of the mouth by application of an effective amount of undecylenic acid and/or the non-toxic salts thereof including the zinc and calcium salts.

It is another object of the present invention to provide methods for reducing and/or eliminating dental plaque, improving gum conditions, reducing and/or eliminating infection and infestations of the mouth including yeast and fungal infections and reducing the incidence of tooth decay due to parasitic bacteria, the methods involving the application of an effective amount of undecylenic acid and/or the non-toxic salts thereof including the zinc and calcium salts.

It is a further object of the invention to provide methods for reducing the bacteria count in the mouth, improving gum conditions, and reducing and preventing plaque on the teeth, the methods contemplating the topical application to at least the teeth and gums of one or more monocarboxylic acids, including undecylenic acid, undecanoic acid, propionic acid, caprylic acid, and caproic acid and/or the non-toxic salts including the calcium and zinc salts thereof.

Other objects and advantages of the invention will become more apparent in light of the following detailed description of the preferred embodiments of the invention.

DESCRIPTION OF THE PREFERRED EMBODIMENTS

The present invention provides methods for reducing, eliminating, and/or preventing the formation of dental plaque on the teeth, the practice of the present methods further improving oral health by causing a reduction, elimination, and/or prevention of infections and infestations of the mouth including those of bacteria, fungal, and yeast origins. Further, the practice of the methods according to the invention reduces the incidence of tooth decay due at least in part to parasitic bacteria, the present methods generally acting to reduce the bacterial count in the mouth to thereby improve and maintain oral health.

While acute infections of the mouth are usually readily detectable and can be treated successfully with antibiotics, most chronic and sub-acute infections are less easily detected and are usually more resistant to standard treatments. Bacterial, fungal, and yeast infections and infestations are virtually always associated with plaque formation on the teeth, such conditions always showing the development of plaque on the gingival margin and between the teeth. The teaching of the present invention involves the reduction, elimination, and/or prevention of plaque formation on the teeth in order to concurrently treat the aforesaid infections and infestations. A further teaching of the present invention involves the observation that an individual who experiences a sudden increase in the incidence of cavities has concurrently experienced a causative change in the bacterial flora of the mouth. In such situations, oral examinations reveal that a plaque exists on the teeth which is substantially identical in appearance to plaque which is associated with chronic gum irritations. The treatment of such conditions must be carefully approached, the use of obvious measures, such as antibiotics often being impossible or contraindicated due to the possibility of allergy or potential resistance or development of resistance to the antibiotic. Treatment is further complicated by the fact that the pathogenic organisms present in the mouth typically fall into a number of differing categories which include organisms of quite differing character and description, thereby generally indicating that a variety of different treatments would be necessary in order to effectively treat the several different categories of pathogens present in the mouth. Such a practice would first necessitate the identification of the certain pathogen or pathogens which were present in the mouth due to both normal and abnormal conditions. Pathogenic microorganisms present in the mouth and which appear to cause the most significant difficulties are summarized as follows:

| | |
|---|---|
| Colon-typhoid | 57% |
| Beta Strep | 19% |
| Hemophilis Para Influenza | 4% |
| Yeast | 7% |
| Fungus | 4% |

Staph infections are also present in a relatively smaller percentage of the population, the oral manifestations of the parasitic staph so encountered being considered to comprise only a portion of the total infestation associated with individuals having such bacteria in the mouth. Yeast infections appear to be increasing, the typical yeast infection being visually identifiable due to the formation of black spots on the necks of the teeth.

According to the practice of the several methods according to the present invention, a monocarboxylic acid substantially selected from the group consisting of undecylenic acid, undecanoic acid, propionic acid, caprylic acid, caproic acid, and/or the non-toxic salts including the calcium and zinc salts thereof is topically applied either directly or in combination with a relatively inert application media, such as a dentifrice paste, to at least the teeth, contact further occurring with the gums and other tissues of the mouth. Of particular utility is the topical application of n-undecylenic acid and/or the non-toxic salts thereof including the calcium and zinc salts. Undecylenic acid, also known as 10-undecenoic acid, is a liquid at room temperature and is typically derived from the destructive distillation of castor oil. Undecanoic acid, also known as hendecanoic acid, is the saturated form of undecylenic acid. A particular teaching of the present invention is that the topical application of the aforesaid acids and salts, particularly undecylenic acid, acts to reduce, control, eliminate, and/or prevent dental plaque on the teeth and to reduce the bacteria count of the mouth, tooth decay due at least in part to parasitic bacteria and gum diseases being markedly reduced through a practice of the present invention. Practice of the present methods further acts to reduce, control, eliminate, and/or prevent yeast infections, fungal conditions, and infections and infestations caused by bacteria, yeast, and fungus in the mouth, the practice of the invention particularly acting to markedly reduce the bacteria count in the mouth. From the standpoint of the individual treated by direct topical application or by use of the aforesaid acids and salts thereof in a dentifrice paste, the most noticeable immediate sign of such treatment is the general subjective feeling of a clean condition in the mouth, a substantial number of individuals reporting that a "fuzzy" feeling present in association with the teeth having been eliminated due to the use of the invention. Such individuals reported that the teeth felt clean and "slick" in a manner similar to the way the teeth feel after mechanical cleaning according to current dental practice. Chronic gum conditions treated according to the present invention can readily be determined by the individual so affected to be progressing toward a more healthy condition. Even conditions associated with stubborn cases of angular Cheilosis-chronic soreness in the corners of the mouth can be improved through a practice of the present invention. In prior dental practice, angular Cheilosis-chronic soreness has been at least partially attributed to vitamin deficiency and has typically been treated through the use of B complex. It is herein disclosed that angular Cheilosis-chronic soreness can be treated, controlled, eliminated and/or prevented through the practice of the present invention without the use of B complex. Experimental usage of the present invention has involved the treatment of a number of selected individual patients, there not having been a single case of irritation or sensitivity having developed due to the practice of the invention either due to direct topical application by a dental practitioner or due to experimental usage of the invention in dentifrice form by the individuals themselves. The clean feeling experienced in the mouth of the individuals treated according to the present invention has also been sufficient to cause the overwhelming majority of the individuals so treated to wish to continue usage of the invention even after the conditions for which the individuals were originally treated had been reduced, controlled, or eliminated. Such continued usage has also proven that the practice of the present invention is a preventative of the conditions noted herein. It is further to be noted from the experimental regimen followed that plaque of all types has been reduced due to the practice of the present invention, virtually all types of plaque being controlled and/or prevented from additional substantial formation.

While the acids and salts utilized in the practice of the present methods can be applied in virtually any strength ranging from even less than 0.01% by weight to full 100% strength applications, such varying applications comprising under differing conditions medically effective amounts, it is considered that the invention is practiced in a preferred manner by utilizing differing percentages of the acids and the salts thereof according to differing modes of treatment. In particular, the direct topical application of the acids and salts according to the present methods by a dental practitioner can vary from a weight proportion of approximately 0.01% when utilized with an oral irrigation device to full 100% strength when directly applied to the teeth and gums in an effort to effect rapid reduction of plaque and/or infections and infestations of the mouth. Such full strength application is preferably followed by irrigation of the mouth. Direct topical application by a dental practitioner typically involves a weight proportion of the acids and/or salts according to the invention in a range of between 10 and 50%, the balance of the applied material being a relatively inert application media. This reduced weight percent is necessitated by a concern for the comfort of the individual due to the fact that the application of the acids and/or salts in full strength produces a harmless burning sensation.

For use in daily oral hygiene, the present invention can be practiced by the provision in a dentifrice, such as a paste, powder, etc., of weight percentages of the acids and/or salts according to the invention of between approximately 0.01 to approximately 10% by weight, the balance of the dentifrice paste, powder, etc., comprising relatively inert components, such as a mild toothpaste, toothpowder, or the like. The invention can further be practiced with oral irrigating devices, the solution so used typically being approximately 0.01% by weight of the acids and/or salts according to the invention. Accordingly, it can be seen that the present invention can be practiced with widely varying weight percentages of the acids and/or salts disclosed herein according to the invention, the method and conditions of application having a particular influence on the proportions of the acids and/or salts utilized in any particular treatment, maintenance, or prevention situation.

Experimental usage of the present invention has produced the following examples which typify treatment according to the invention and the results provided thereby.

EXAMPLE I

The patient evidenced acute gum infection and a heavy, yellow, grainy plaque. Culture revealed Enterobacter, Klebsiella group; the patient was treated with antibiotic to reduce acute infection. Following such infections an inflammation typically lingers, treatment of which is impossible with antibiotics for a prolonged period of time in the mouth since exposure to mucous membrane eventually causes allergic reaction to an antibiotic. When the acute stage was past, treatment with antibiotics was discontinued and a dentifrice paste comprised of 2% by weight of undecylenic acid and 2% by weight of zinc undecylenate was applied twice daily coincidental with the regular brushing of the teeth. Chronic inflammation subsided immediately, the plaque disappearing as the inflammation disappeared.

EXAMPLE II

The patient had a long-standing chronic gum condition with two areas of deep damage to bone between teeth, light plaque between the teeth, bleeding gums, and a poor prognosis. Culture revealed Haemophilus Parainfluenzae, a rare organism to find in the mouth. Home use of the dentifrice paste described in Example I dramatically controlled the wide-spread chronic inflammation. The two deep areas required antibiotic irrigation for control. When the two deep areas were brought under control with antibiotic irrigation and use of the paste, home care with the paste alone has been sufficient to control both the plaque and the widespread chronic inflammation and the two deep areas. No measurable bone loss has occurred since treatment began.

EXAMPLE III

The patient had extensive dental decay with fillings in all teeth, cavities appeared with such rapidity that patient had to be recalled every three months for filling of caries. A medium growth of yellow-white plaque was always present even with normal mechanical cleaning. Patient had an average of six new cavities every three months. Cultures revealed only normal flora although some identified microorganism or microorganisms were suspected to be present in addition to the plaque. Patient began use of the dentifrice paste described in Example I and continues use of the paste. Cavities slowly regressed until periodic checks were necessary only every six months, only about three new cavities now occurring every six months. The plaque is still visible in rough areas of old fillings but has been substantially reduced on all portions of the teeth since use of the dentifrice paste began.

EXAMPLE IV

The patient was found to have cancer of the left tonsilar arch. Treatment of choice was radiation; this is a procedure normally requiring extraction of all of the teeth. Under such conditions, teeth are normally extracted due to the altered flora of the mouth occurring due to radiation which causes the teeth to decay so badly that repair is essentially impossible. Teeth under such conditions literally fall apart. Additionally, the altered blood supply to the jaw bones, especially the mandible, which is caused by radiation treatments usually causes death of the bone if an extraction is necessary after the blood supply has been so affected. The patient was radiated, the tumor regressed and has not recurred. After radiation, patient experienced black dots on the teeth which quickly became cavities. A dentifrice paste such as described in Example I was used in combination with Nilstat Cream and massaged into the teeth and gums three times a day. Treatment caused stoppage of the black dots and decay. Treatment with Nilstat Cream was discontinued with continued usage of the present dentifrice paste, there being no significant decay subsequently, no loss of teeth, and no adverse conditions indicative of a reduced level of oral health.

EXAMPLE V

The patient bothered by very sore gums with essentially no visible symptoms. Gum tissues appeared slightly scalded, whitish, but without the usual appearance of acute infection. A substantial amount of plaque was present on the teeth. Culture revealed E. coli, not a rare infection, but one not usually seen in the mouth. Dentifrice paste formulated substantially as described in Example I was immediately begun without use of antibiotics. The tenderness of the gums disappeared in less than four days. Plaque further disappeared within four days, the teeth appearing quite clean. Inflammation completely disappeared within ten days without recurrence. Patient continues use of the dentifrice paste.

EXAMPLE VI

An overweight young woman in poor general health evidenced acute red swelling of the gums and sore mouth, plaque appearing in all inflamed areas with a thickness such as to appear pustular. Culture revealed Enterococcus gp. D. Initial treatment involved tetracycline mouth wash and internal tetracycline. Acute soreness and most of the redness disappeared within five days, gums remaining puffy and swollen. Patient began use of dentifrice paste as substantially described in Example I, the teeth being cleaned up immediately and the swollen tissues slowly returning to normal after three weeks usage of the dentifrice paste. When the patient discontinued use of the paste, the swelling reappeared within a week. Use of the paste was again begun without recurrence of swelling and inflammation.

EXAMPLE VII

The patient evidenced chronic inflammation of unusual nature. While tissues were not sore, the tissues were a bright red and swollen. A great deal of bone damage existed in certain areas, as if an organism had found a particular invasion location at which deep pockets were formed resulting in two loose teeth. Culture revealed pure pneumococcus, apparently of long standing. Heavy plaque existed on the teeth. Tetracycline was started as a mouthwash and also internally to prevent the organism from relocating in the throat or lungs. After passage of the acute stage, the deep pockets were surgically treated to obliterate room for infection. Plaque changed in appearance to a heavy line around the necks of the teeth which would reappear within 30 minutes after brushing. Treatment with dentifrice paste as substantially described in Example I was begun, the plaque disappearing immediately. General health of the mouth has since been excellent, there being no recurrence of the acute or chronic infection.

EXAMPLE VIII

The patient had a chronic irritation and many cavities. Heavy plaque recurred quickly after normal cleaning. Patient complained of teeth feeling "dirty" all the time. Culture revealed Staph Aurens. Antibiotic therapy quickly stopped the mild soreness and chronic irritation. Plaque changed but remained. Patient felt that plaque was lessened and did not return quite as quickly. Fillings were placed and the original irritation slowly reappeared before the fillings were finished over a period of weeks. Plaque again became heavier. Treatment with dentifrice according to the invention was begun, the plaque disappearing in a matter of days. Patient has continued use of the paste without recurrence of irritation and with a reduced level of cavities.

EXAMPLE IX

The patient constantly bothered with cavities around the necks of most of the teeth. Teeth had so many fillings that new cavities were difficult to find. Medium plaque recurred quickly after normal cleaning and was very difficult to brush away. Culture revealed Enterococcus which was treated experimentally with Lincocin mouthwash. Plaque remained. Antibiotic Garamycin cream was applied three times daily, the plaque gradually being reduced. As soon as the antibiotic cream was discontinued, plaque reappeared. Patient developed sensitivity to antibiotic cream, it being necessary to discontinue use thereof. Use of the dentifrice paste according to the invention was begun, the plaque disappearing immediately. Patient has been able to remain on the paste over a period of years, cavities around the necks of the teeth being diminished in number during this period of time by over 75%.

EXAMPLE X

The patient evidenced chronically sore mouth, a few fillings and cavities, and severe bone damage in isolated places apparently due to bacterial activity having a local foot-hold and invading deeply into the tissues. Culture revealed Beta Strep. Plaque was obvious between the teeth and around the necks of the teeth, but had apparently done little damage to the teeth themselves. Infection control with antibiotics, both as a mouthwash and internally to prevent the strep infection from settling elsewhere. Gingivectomies were performed on the damaged areas. A dentifrice paste prepared according to the invention was used after the surgery, plaque disappearing immediately. Since the surgery and with continued use of the dentrifrice paste, no further irritation or damage to the bone has occurred. The mouth is now completely clean and healthy, it being believed, however, that former gum problems would return if the use of the paste were discontinued due to other health problems of the patient.

EXAMPLE XI

The patient subject to three month oral examinations due to rampant caries. A high rate of decay existed, approximately four cavities having to be filled every three months. Teeth covered absolutely with a grainy plaque which would recur immediately after cleaning. The plaque was a yellow-white which could be scraped from the teeth at any location, no success being enjoyed in controlling the plaque even though antibiotics, antifungus medicines, and other techniques were employed. Patient began use of the dentifrice paste prepared according to the invention on a daily basis at home, there being an immediate reduction in the amount of plaque on the teeth. The incidence of decay diminished constantly for over a year until the cavity level now requires only one filling every three months. The plaque is substantially reduced, although not completely eliminated, and the health of the gum has improved. An unknown microorganism is suspected which has not been eliminated by the use of the paste but which has been substantially controlled.

EXAMPLE XII

The patient evidenced very heavy plaque, red gum tissue which was swollen and hypertrophied in places to such an extent that a gingival papilla would be loose for half an inch and would pull away from the tooth and stand away until pushed back. Many cavities were present on surfaces which had no attrition, portions of the teeth eroding for no apparent reason. Culture revealed Candida. Treatment with a dentifrice paste according to the invention was started, plaque diminishing immediately. Cavities were filled and rough eroded places filled to eliminate places in which the Candida could live. Hypertrophied tissues became less red and irritated, but did not completely return to normal. Plaque evident in places between teeth and under hypertrophied tissues. Hypertrophied tissues then removed with surgery and use of the dentifrice paste continued. Plaque diminished markedly, but still evident between teeth. Patient presently experiences little decay and no tissue hypertrophy with continued use of the dentifrice paste. Plaque diminished in direct ratio to home care with the paste, meticulous use of the paste for even short periods of time causing the plaque to disappear and not recur.

EXAMPLE XIII

A child of 12 with no history of dental decay was suddenly observed to have a total of seven cavities. A medium growth of white plaque was in evidence. Culture revealed Budding Yeast. Treatment with dentifrice paste as previously described was begun and cavities filled. Subsequent examination revealed a clean set of teeth with no cavities and no plaque. Patient now evidencing cavities which invariably accompany diet and eating habits of typical teenage individuals. Without original and continued treatment according to the present invention, it is believed that the high rate of decay first evidenced at the age of 12 would have continued.

While the foregoing provides typical examples of individuals treated according to the present invention, it is to be understood that the examples provide only a representative sampling of an experimental program involving over 1,000 individuals treated either with the dentifrice paste as described hereinabove, by direct topical application by a dental practitioner, or with oral irrigation. In the experimental program, not a single case of irritation or sensitivity has developed. Individuals continuing to use the dentifrice paste on an experimental home program report the feeling of having a "clean" mouth which has been unobtainable by any other program of oral treatment. The practice of the present invention in the experimental program so described has not resulted in a single example where plaque has not been reduced, all of the individuals so treated having been positively aided to at least some degree. While the acids and/or salts, particularly in undecylenic acid and the zinc and calcium salts thereof, have long been known, the results provided by a practice of the methods according to the invention are completely unexpected and would not have been an obvious result of such treatment to a person of ordinary skill in the art. Accordingly, the present invention is seen to provide novel methods of effecting the beneficial results referred to hereinabove.

The foregoing is considered as illustrative only of the principles of the invention. Further, since numerous modifications and changes will readily occur to those skilled in the art, it is not desired to limit the invention to the exact practice shown and described, and accordingly, all suitable modifications and equivalents may be resorted to, falling within the scope of the invention.

What is claimed as new is as follows:

1. A method for reducing dental plaque and pellicle precursor of plaque comprising brushing or irrigating the teeth with a dental preparation containing an active ingredient, the active ingredient consisting essentially of 2% by weight of undecylenic acid and 2% by weight of zinc undecylenate.

* * * * *